(12) United States Patent
Yang et al.

(10) Patent No.: US 11,828,715 B2
(45) Date of Patent: Nov. 28, 2023

(54) SOIL HUMIDITY MICROWAVE REMOTE SENSING DEVICE WITH MULTI-MODE COMPATIBILITY VIA GNSS-R AND A METHOD OF USING THE SAME

(71) Applicant: Shandong Orientation Electronic Technology Co., Ltd., Jining (CN)

(72) Inventors: Dongkai Yang, Jining (CN); Mutian Han, Jining (CN); Haining Chang, Jining (CN)

(73) Assignee: SHANDONG ORIENTATION ELECTRONIC TECHNOLOGY CO., LTD., Jining (CN)

( * ) Notice: Subject to any disclaimer, the term of this patent is extended or adjusted under 35 U.S.C. 154(b) by 561 days.

(21) Appl. No.: 17/131,210

(22) Filed: Dec. 22, 2020

(65) Prior Publication Data
US 2021/0285895 A1   Sep. 16, 2021
US 2022/0136983 A9   May 5, 2022

(30) Foreign Application Priority Data
Mar. 13, 2020   (CN) .......................... 202010175258.0

(51) Int. Cl.
*G01N 22/04* (2006.01)
*H01Q 9/04* (2006.01)

(52) U.S. Cl.
CPC .......... *G01N 22/04* (2013.01); *H01Q 9/0428* (2013.01)

(58) Field of Classification Search
CPC .... G01N 22/04; G01N 27/221; G01N 33/246; H01Q 9/0428
See application file for complete search history.

(56) References Cited

U.S. PATENT DOCUMENTS

2018/0180742 A1*   6/2018   Capet ...................... G01S 19/36

FOREIGN PATENT DOCUMENTS

| CN | 101266292 | * | 9/2008 |
| CN | 101377542 | * | 10/2011 |

OTHER PUBLICATIONS

Liyan, GNSS-IRDdual-frequency Data Fusion Surface Soil Moisture Retrieval, Thesis paper, Jan. 15, 2020, Shandong Agricultural University, China (Year: 2020).*

(Continued)

*Primary Examiner* — Christopher E Mahoney
(74) *Attorney, Agent, or Firm* — Scully, Scott, Murphy & Presser, P.C.

(57) ABSTRACT

The disclosure relates to the technical field of soil humidity measurement, in particular to a soil humidity microwave remote sensing device with multi-mode compatibility via GNSS-R and a method of using the same. The device includes a direct RHCP antenna, reflective RHCP antenna, a reflective LHCP antenna, a combiner, switches, preamplifiers, down-conversion modules, sampling and quantizing modules, a capturing and closed-loop tracking module, an open-loop tracking module, a position calculating and controlling module and a soil humidity inverting module. The soil humidity microwave remote sensing device with multi-mode compatibility via GNSS-R realizes flexibly switching among different GNSS-R soil humidity microwave remote sensing working modes, so that the soil remote sensing device can fully utilize advantages of the different working modes to realize compatible multi-mode observation. The method realizes multi-mode, non-contact and large-area soil humidity measurement by utilizing the GNSS reflected signals.

3 Claims, 5 Drawing Sheets

(56) References Cited

OTHER PUBLICATIONS

Alonso-Arroyo, Improving the Accuracy of Soil Moisture Retrievals Using the Phase Difference of the Dual-Polarization GNSS-R Interference Patterns, IEEE Geoscience and Remote Sensing Letters, vol. 11, No. 12, Dec. 2014.*

Egido, Global Navigation Satellite Systems Reflectometry as a Remote Sensing Tool for Agriculture, Remote Sensing ISSN 2072-4292 Remote Sens. 2012, 4, 2356-2372; doi:10.3390/rs4082356.*

* cited by examiner

SOIL HUMIDITY MICROWAVE REMOTE SENSING DEVICE WITH MULTI-MODE COMPATIBILITY VIA GNSS-R AND A METHOD OF USING THE SAME

CROSS REFERENCE TO RELATED APPLICATIONS

This patent application claims the benefit and priority of Chinese Patent Application No. 202010175258.0 filed on Mar. 13, 2020, the disclosure of which is incorporated by reference herein in its entirety as part of the present application.

BACKGROUND

The present disclosure relates to the technical field of soil humidity measurement, in particular to a soil humidity microwave remote sensing device with multi-mode compatibility via GNSS-R and using method thereof.

Soil humidity is an important component of water circulation balance and affects the sensible and latent heat flux from the earth's surface to the atmosphere. In a large scale space, these fluxes can affect the weather pattern. In local areas, the availability of surface humidity is critical to plant growth. Soil humidity also affects drought and rainfall, and plays an important role in climate change. Therefore, monitoring long-term changes of soil humidity is of great significance for carbon cycling and agriculture.

The existing soil humidity monitoring means can be mainly divided into contact type measuring means and non-contact type measuring means. The contact type measuring means is the most accurate and stable, but the measuring process can damage the soil structure. In general, a measurement can only represent soil humidity in an area range of ten and some square centimeters around a point measured, and cannot represent the soil humidity in a large area. The non-contact measurement means mainly include active and passive satellite-borne microwave remote sensing means, which achieve large-area non-contact measurement, but the resolution of time and space is poor, and the cost of development and maintenance is high.

With the development of Global Navigation Satellite System (GNSS), GNSS-Reflectometry (GNSS-R) remote sensing technology emerged, which uses navigation signals emitted from GNSS satellites and navigation signals reflected from soil to measure soil humidity. Due to the large number of GNSS navigation satellites, there are many signal sources, and navigation signals can be freely acquired in the global scope; further, the development of direct and reflected signals receiving and processing device can be carried out on the basis of the existing mature GNSS receiver, so the GNSS-R technology can realize soil humidity monitoring with low cost and high space and time resolution. At present, the GNSS-R soil humidity measurement technology has two modes, one is discrete mode, and another is interference mode. In the discrete mode, the receiving and processing device receives GNSS direct signals and soil reflected signals by using two or more independent antennas, respectively, each antenna occupies a separate processing channel and soil humidity can be obtained by performing an inversion process on signals received by all the antennas, as mentioned in the Chinese patent application No. 2014108164014 entitled "Measuring Device and Measuring Method for Regional Soil Humidity via GNSS-R", and the Chinese patent application No. 2015100723626 entitled "Soil Humidity Detecting Device via GNSS-R assisted by a Temperature Sensor". This mode has better measuring performance when the satellite elevation angle is higher, since the signal-to-noise ratios of the reflected signals are high at high elevation angles of the satellite. In the interference mode, the receiving and processing device only uses one antenna to simultaneously receive direct and soil reflected signals, which utilizes an interference effect between the direct signals and the soil reflected signals, as mentioned in the Chinese patent application No. 2016103438553 "Soil Humidity Measuring Method based on Interference Power Peak-valley Value via GNSS", the Chinese patent application No. 2018103444498 entitled "Soil Humidity Monitoring Method and Device based on Multiband Blending via GNSS-IR", the Chinese patent application No. 2015108193933 entitled "Method for Estimating Soil Humidity Using Signal-to-noise Ratio Grade Data via GPS", and the Chinese patent application No. 2014102755487 entitled "Soil Humidity Inversion Method based on Low Elevation Signals Received by a Beidou Base Station". This mode has better measuring performance when the satellite elevation angle is lower, since the signal-to-noise ratios of the interference signals are higher at low elevation angles of the satellite. Therefore, the single-mode GNSS-R receiving and processing device has low utilization rate of satellite data. Moreover, because the high elevation angle operation and the low elevation angle operation of the satellite are respectively performed at different periods, the time resolution of the GNSS-R receiving and processing device in a single mode is not high enough, and seamless soil humidity measurement cannot be realized.

BRIEF DESCRIPTION

In order to solve the above technical problems, the embodiments of the present disclosure aim to provide a soil humidity microwave remote sensing device with multi-mode compatibility via GNSS-R and a method of using the same, which can use advantages of different working modes to realize the function of observing in compatible multiple modes.

The technical solutions adopted by the present disclosure for solving the technical problem are as follows.

A soil humidity microwave remote sensing device with multi-mode compatibility via GNSS-R includes a direct right-hand circularly polarized (RHCP) antenna, configured for receiving a GNSS direct signal from a satellite, a reflective RHCP antenna, configured for receiving a right-handed component signal of a GNSS signal reflected by soil, a reflective left-hand circularly polarized (LHCP) antenna, configured for receiving a left-handed component signal of the GNSS signal reflected by the soil, a combiner, configured for summing the signals from the direct RHCP antenna, the reflective RHCP antenna and the reflective LHCP antenna, switches, configured for being controlledly switched, to enable the direct RHCP antenna, the reflective RHCP antenna and the reflective LHCP antenna to be switched, preamplifiers, configured for performing power amplification and noise suppression on signals captured by the direct RHCP antenna, the reflective RHCP antenna and the reflective LHCP antenna, which are analog radio frequency signals, down-conversion modules, configured for downconverting the analog radio-frequency signals to analog intermediate-frequency signals, sampling and quantizing modules, configured for converting the analog intermediate frequency signals into digital intermediate frequency signals, a capturing and closed-loop tracking module, configured for processing digital intermediate frequency signal associated with the GNSS direct signal, to measure parameters of the digital intermediate frequency signal associated with the GNSS direct signal and demodulate a navigation message and outputting the measured parameters such as frequency and phase to open-loop tracking modules, open-loop tracking modules, configured for tracking the digital intermediate-frequency signal associated with the right-handed component signal or the left-handed component signal and measuring correlation power, a position calculating and controlling module, configured for calculating positions of the device and the satellite by utilizing information received from the capturing and closed-loop tracking module, and controlling switching of the switches according to predetermined parameters so as to flexibly switching among different working modes, and a soil humidity inverting module, configured for measuring a soil humidity by the measured signal.

In some embodiments, the direct RHCP antenna is an omnidirectional antenna, the reflective RHCP antenna is a high-gain, narrow-beam antenna, and the reflective LHCP antenna is a high-gain, narrow-beam antenna.

A method of using the soil humidity microwave remote sensing device with multi-mode compatibility via GNSS-R has a single-antenna interference mode, a dual-antenna interference mode, a dual-antenna discrete mode, and a three-antenna discrete mode.

In the single-antenna interference mode, the method includes operations of controlling the switches by the position calculating and controlling module to disable the reflective RHCP antenna and the reflective LHCP antenna, and only enable direct RHCP antenna, passing an interference signal through corresponding one of the preamplifiers, corresponding one of the down-conversion modules, corresponding one of the sampling and quantizing modules, the capturing and closed-loop tracking module in sequence to obtain power information of the interference signal, performing position calculation by the position calculating and controlling module using the interference signal to obtain position information of the device and information about an elevation angle and an azimuth angle of the satellite, and performing an inversion process on the power information of the interference signal by the soil humidity inverting module to obtain a soil humidity.

In the dual-antenna interference mode, the method includes operations of controlling the switches by the position calculating and controlling module to enable the reflective LHCP antenna and the direct RHCP antenna, passing the GNSS direct signal and the left-handed component signal through the combiner to obtain an interference signal, passing the interference signal through corresponding one of the preamplifiers, corresponding one of the down-conversion modules, corresponding one of the sampling and quantizing modules, the capturing and closed-loop tracking module in sequence to obtain power information of the interference signal, performing position calculation by the position calculating and controlling module using the interference signal to obtain position information of the device and information about an elevation angle and an azimuth angle of the satellite, and performing an inversion process on the power information of the interference signal by the soil humidity inverting module to obtain a soil humidity.

In the dual-antenna discrete mode, the method includes operations of controlling the switches by the position calculating and controlling module to enable the reflective LHCP antenna and the direct RHCP antenna, passing the GNSS direct signal through corresponding one of the preamplifiers, corresponding one of the down-conversion modules, corresponding one of the sampling and quantizing modules, the capturing and closed-loop tracking module in sequence to obtain a code phase, a carrier phase, and correlation power information of the GNSS direct signal, wherein the code phase and the carrier phase are used to assist the open-loop tracking module in tracking the left-handed component signal in an open-loop manner to obtain correlation power information of the left-handed component signal, performing position calculation by the position calculating and controlling module using the GNSS direct signal to obtain position information of the device and information about an elevation angle and an azimuth angle of the satellite, and performing an inversion process on the correlation power information of the GNSS direct signal and the correlation power information of the left-handed component signal by the soil humidity inverting module to obtain a soil humidity.

In the three-antenna discrete mode, the method includes operations of controlling the switches by the position calculating and controlling module to enable the direct RHCP antenna, the reflective LHCP antenna and the reflective RHCP antenna, passing the GNSS direct signal through corresponding one of the preamplifiers, corresponding one of the down-conversion modules, corresponding one of the sampling and quantizing modules, and the capturing and closed-loop tracking module in sequence to obtain a code phase, a carrier phase, and correlation power information of the GNSS direct signal, wherein the code phase and the carrier phase is used to assist the open-loop tracking module in tracking the right-handed component signal and the left-handed component signal in an open-loop manner to obtain correlation power information of the right-handed component signal and correlation power information of the left-handed component signal, performing position calculation by the position calculating and controlling module using the GNSS direct signal to obtain position information of the device and information about an elevation angle and an azimuth angle of the satellite, and performing an inversion process on the correlation power information of the GNSS direct signal, the correlation power information of the left-handed component signal, and the correlation power information of the right-handed component signal by the soil humidity inverting module to obtain a soil humidity.

Compared with the prior art, the disclosure has the following beneficial effects.

The soil humidity microwave remote sensing device with multi-mode compatibility via GNSS-R provided in some embodiments realizes flexibly switching among different GNSS-R soil humidity microwave remote sensing working modes, so that the soil humidity remote sensing device can fully utilize the advantages of different working modes to realize compatible multi-mode observation. The device realizes soil humidity measurement in multiple modes, in non-contact manner and at large area by utilizing the GNSS reflected signal.

DETAILED DESCRIPTION

The following further describes the embodiments of the present disclosure:

Example 1

Figure 1:
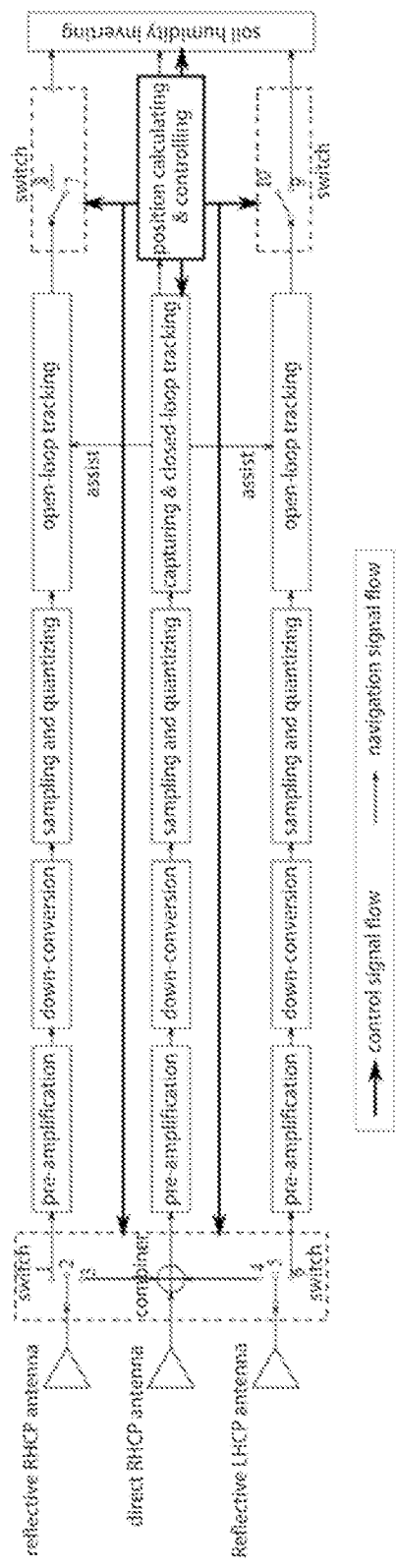
FIG. 1 is a block diagram of a configuration of the present disclosure.

As shown in FIG. 1, a soil humidity microwave remote sensing device with multi-mode compatibility via GNSS-R includes a direct RHCP antenna, a reflective RHCP antenna, a reflective LHCP antenna, a combiner, switches, preamplifiers, down-conversion modules, sampling and quantizing modules, a capturing and closed-loop tracking module, open-loop tracking modules, a position calculating and controlling module, and a soil humidity inverting module.

The direct RHCP antenna is configured for receiving a GNSS direct signal from a satellite.

The reflective RHCP antenna is configured for receiving a right-handed component of a GNSS signal reflected by soil.

The reflective LHCP antenna is configured for receiving a left-handed component of the GNSS signal reflected by soil.

The combiner is configured for summing signals from the direct RHCP antenna, the reflective RHCP antenna, and the reflective LHCP antenna.

The switches are configured for being controlledly switched, so that the direct RHCP antenna, the reflective RHCP antenna and the reflective LHCP antenna can be switched.

The preamplifiers are configured for performing power amplification and noise suppression on analog radio-frequency signals captured by the direct RHCP antenna, the reflective RHCP antenna, and the reflective LHCP antenna.

The down-conversion modules are configured for down-converting the analog radio-frequency signals to analog intermediate-frequency signals.

The sampling and quantizing modules are configured for converting the analog intermediate-frequency signals into digital intermediate-frequency signals.

The capturing and closed-loop tracking module is configured for processing digital intermediate frequency signal associated with the GNSS direct signal to measure parameters of the digital intermediate frequency signal associated with the GNSS direct signal and demodulate a navigation message which is output and used for calculating positions of the device and the satellite, and output the measured parameters such as frequency and phase to the open-loop tracking modules so as to assist in tracking of the reflected signals.

The open-loop tracking modules are configured for tracking the digital intermediate-frequency signal associated with the right-handed component signal or the left-handed component signal and measuring correlation power.

The position calculating and controlling module is configured for calculating positions of the device and the satellite by utilizing the information received from the capturing and the closed-loop tracking module, and controlling the switching of the switches according to predetermined parameters so as to flexibly switch among different working modes.

The soil humidity inverting module is configured for measuring the soil humidity by means of the measured interference signals or discrete signals.

The direct RHCP antenna is an omnidirectional antenna, the reflective RHCP antenna is a high-gain, narrow-beam antenna, and the reflective LHCP antenna is a high-gain, narrow-beam antenna.

Example 2

A method of using the soil humidity microwave remote sensing device with multi-mode compatibility via GNSS-R has a single-antenna interference mode. In this mode, the position calculating and controlling module controls the switches to close contacts 2, 5, 7, and 10, so as to disable the reflective RHCP antenna and reflective LHCP antenna, and only direct antenna RHCP is enabled. In this mode, the GNSS direct signal interferes with the GNSS signal reflected from soil at the direct RHCP antenna to form an interference signal. The interference signal is subject to the processes of the preamplifier, the down-conversion module, the sampling and quantizing module, the capturing and closed-loop tracking module in order, to obtain power information of the interference signal. After that, the position calculating and controlling module uses the interference signal to calculate position to obtain the position information of the device and information about the elevation angle and an azimuth angle of the visible navigation satellite. Finally, the soil humidity inverting module performs an inversion process on the power information of the interference signal to obtain the soil humidity.

In this mode, the power information of interference signal measured by the device according to the present disclosure can be expressed as:

$$P(\theta) = P_d(\theta) + P_{rr}(\theta) + 2\sqrt{P_d(\theta)P_{rr}(\theta)} \cos\left(\frac{4\pi H \sin(\theta)}{\lambda} + \varphi_0\right) \quad (1)$$

In expression (1), $\theta$ is an elevation angle of the navigation satellite, $P(\theta)$ is power of the interference signal, $P_d(\theta)$ is power of the direct signal, $P_{rr}(\theta)$ is power of the RHCP component of the reflected signal, H is height of the direct RHCP antenna relative to soil surface, $\lambda$ is a wavelength of the navigation signal, and $\varphi_0$ is an initial phase of the interference signal.

The soil humidity $m_v$ has an effect on the power $P_{rr}(\theta)$ of the RHCP component of the reflected signal, and in turn affects the power $P(\theta)$ of the interference signal, $P_{rr}(\theta)$ may be further expressed as:

$$P_{rr}(\theta) = P_d(\theta)\Gamma_{rr}(\theta) \quad (2)$$

In expression (2), $\Theta_{rr}(\theta)$ is the RHCP component of a reflectivity of the GNSS signal at an elevation angle $\theta$ of the satellite, which can be expressed by the following equation:

$$\Gamma_{rr}(\theta) = \frac{(1-\varepsilon_r)^2\cos^4(\theta)}{\left(\sin(\theta)+\sqrt{(\varepsilon_r-\cos^2(\theta))}\right)^2} \tag{3}$$

$$\left(\varepsilon_r\sin(\theta)+\sqrt{(\varepsilon_r-\cos^2(\theta))}\right)^2$$

In expression (3), $\varepsilon_r$ is a relative permittivity of soil, which is a function of soil humidity $m_v$ and can be represented by the following empirical model:

$$\varepsilon_r = 2.8603 + 3.7463 \times m_v + 119.1755 \times m_v^2 \tag{4}$$

Figure 2:
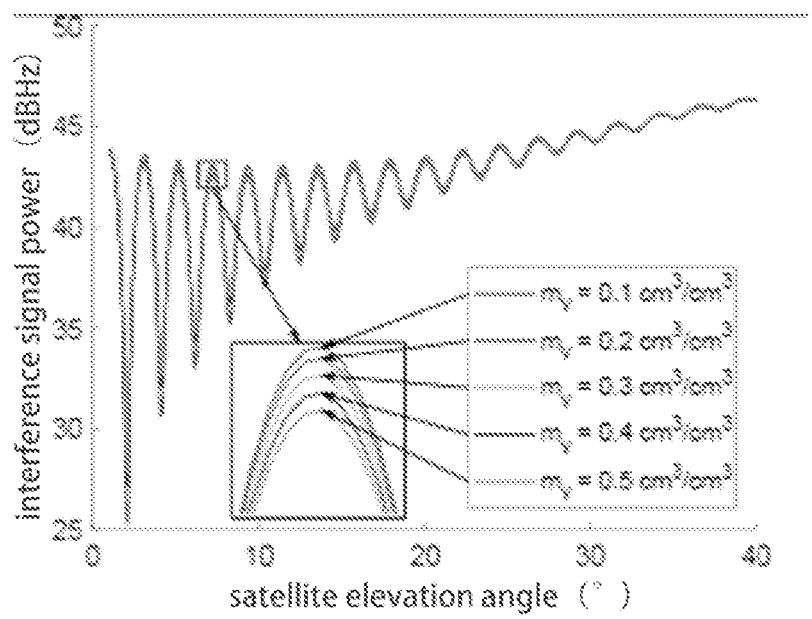
FIG. 2 is a schematic diagram of an effect of soil humidity on power of an interference signal (RHCP) according to the present disclosure.

The above expressions (1) to (4) establish a quantitative relationship between the soil humidity and the power of the interference signal measured by the device of the present disclosure in this mode. FIG. 2 shows variation of the power of the interference signal with the elevation angle of navigation satellite at different soil humidities.

It can be seen from FIG. 2 that curve representing power of the interference signal exhibits regular oscillation as the elevation angle of satellite changes. When the soil humidity increases, the oscillation amplitude of the power of the interference signal decreases, and the soil humidity inverting module can perform inversion according to the oscillation amplitude to obtain soil humidity. The existing soil humidity inversion technology firstly performs low-level (usually second or third order) polynomial fitting on the power of the interference signal. This process can model a trend term of the power of the interference signal. Then, the trend term is removed from the interference signal, to obtain a power of the interference signal without the trend term, which can be described by the following formula:

$$dP = A(\theta)\cos\left(\frac{4\pi H\sin(\theta)}{\lambda} + \varphi_0\right) \tag{5}$$

In expression (5), $A(\theta)$ is a oscillation amplitude of the power of interference signal, which varies with the elevation angle of the satellite. Existing technology assumes that $A(\theta)$ is constant, and a standard cosine function is employed to model the power of the interference signal after removing the trend term, and the oscillation amplitude A of the power of the interference signal can be estimated by the least square fitting. The variation of the oscillation amplitude A of the power of the interference signal with the soil humidity is shown in FIG. 3.

Figure 3:
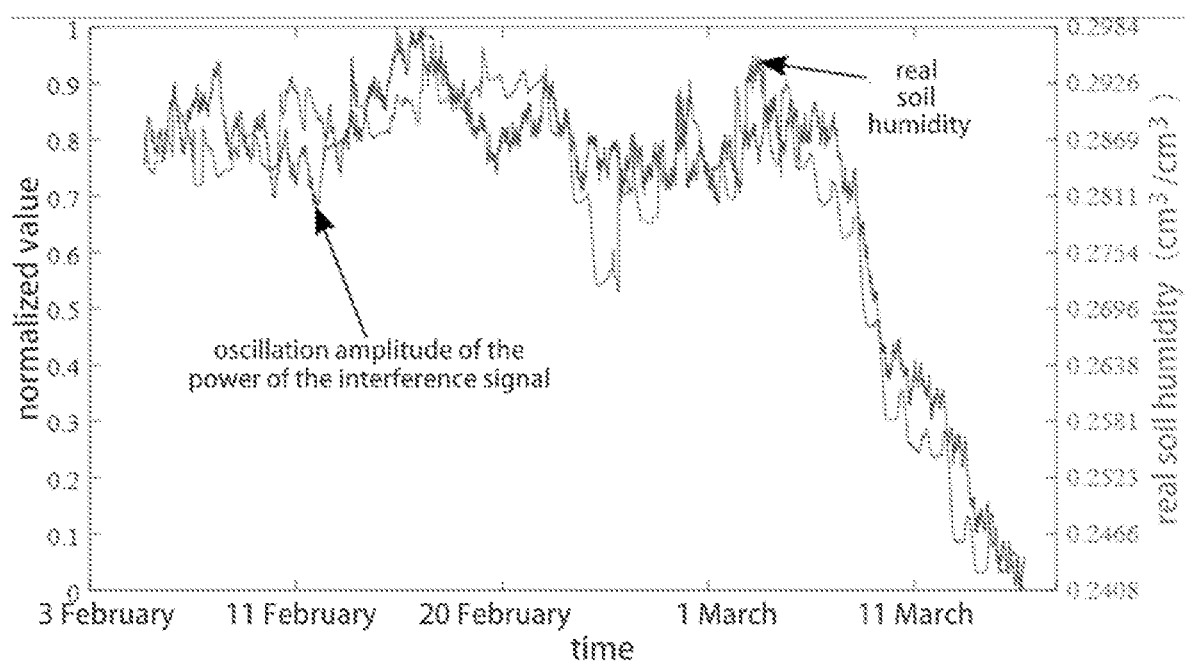
FIG. 3 is a schematic diagram of variation of oscillation amplitude of the interference signal (RHCP) power with the soil humidity according to the present disclosure.

In FIG. 3, both the oscillation amplitude (after flipping) of the power of the interference signal and the real soil humidity are normalized as shown in a left Y axis, and the corresponding real value of the soil humidity is shown in a right Y axis. It can be seen from the figure that the variation of the power amplitude of the interference signal is consistent with the variation of the real soil humidity.

Example 3

The method of using soil humidity microwave remote sensing device with the multi-mode compatibility via GNSS-R has a dual-antenna interference mode.

In this mode, the position calculating and controlling module controls the switches to close the contacts 2, 4, 7, 10, to enable the reflective LHCP antenna. In this case, the LHCP component of the reflected signal and direct signal firstly form the interference signal through a combiner. Then, the interference signal is subject to the processes of the preamplifier, the down-conversion module, the sampling and quantizing module, the capturing and closed-loop tracking module successively to obtain power information of the interference signal. After that, the position calculating and controlling module uses the interference signal to calculate position to obtain the position information of the device and the information about the elevation angle and azimuth angle of the visible navigation satellite. Finally, the soil humidity inversion module can employ existing technology to perform the inversion process on the power information of the interference signal to obtain the soil humidity.

The basic principle of the dual-antenna interference mode is the same as that of the single antenna interference mode. The only difference is in that it is the LHCP component of the reflected signal which interferes with the direct signal, rather than the RHCP component. Therefore, a quantitative relationship between the soil humidity and the interference signal in the mode can be obtained by only replacing subscript rr in the extensions (1) to (3) with rl, and the resultant $P_{rl}(\theta)$ represents the LHCP component of the reflected signal. $\Gamma_{rl}(\theta)$ is a LHCP component of the reflectivity of the GNSS signal at different satellite elevation angles, which can be expressed by the following expression:

$$\Gamma_{rl}(\theta) = \frac{(\varepsilon_r-1)^2\sin^2(\theta)(\varepsilon_r-\cos^2(\theta))}{\left(\sin(\theta)+\sqrt{(\varepsilon_r-\cos^2(\theta))}\right)^2} \tag{6}$$

$$\left(\varepsilon_r\sin(\theta)+\sqrt{(\varepsilon_r-\cos^2(\theta))}\right)^2$$

Figure 4:
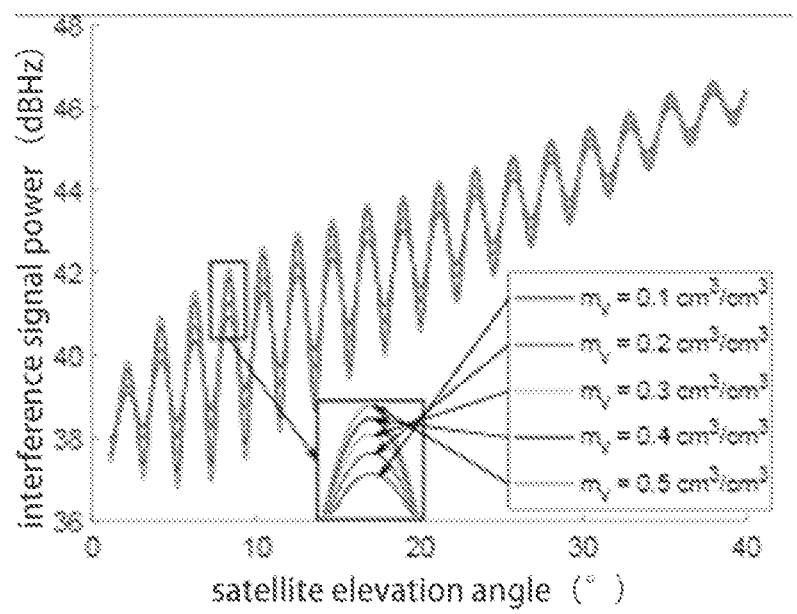
FIG. 4 is a schematic diagram of an effect of soil humidity on power of an interference signal (LHCP) according to the present disclosure.

FIG. 4 shows the variation of the power of the reference signal with the elevation angle of the navigation satellite at different soil humidities in this mode.

It can be seen from FIG. 4 that the oscillation amplitude of the power of the interference signal increases when the soil humidity increases. The soil humidity inverting module can perform soil humidity inversion accordingly. The inversion method is similar to the single-antenna interference mode, and reference can be made to the existing technology.

Example 4

The method of using the soil humidity microwave remote sensing device with multi-mode compatibility via GNSS-R has dual-antenna discrete mode.

In this mode, the position calculating and controlling module control the switches to close the contacts 2, 6, 7, 9, to enable the reflective LHCP antenna. In this case, the direct signal is subject to the processes of the preamplifier, down-conversion module, the sampling and quantizing module, the capturing and closed-loop tracking module in order, to obtain information about a code phase, a carrier phase, and correlation power of the direct signal. The information about the code phase and the carrier phase is used to assist the open-loop tracking module to perform the open-loop tracking on the LHCP component of the reflected signal and obtain the correlation power information of the LHCP component of the reflected signal. After that, the position calculating and controlling module uses direct signal to calculate position to obtain the position information of the device and information of the elevation angle and azimuth angle of the visible navigation satellite. Finally, the soil humidity inverting module can use the existing technology to perform the inversion process on the correlation power information of the direct signal and the correlation power information of the LHCP component of the reflected signal to obtain the soil humidity.

In this mode, the correlation power of the direct signal measured by the device is represented by $P_d(t)$ and the correlation power of the LHCP component of the reflected signal measured by the device is represented by $P_{rl}(t)$. The waveform shapes of the correlation powers of the direct and reflected signal are determined by the autocorrelation function of the navigation signal, and the autocorrelation function $R(\tau)$ of the navigation signal can be described by the following expression:

$$R(\tau) = \begin{cases} \left(1 - \dfrac{\tau}{T_c}\right)^2, & |\tau| \le T_c \\ 0, & |t| > T_r \end{cases} \quad (7)$$

In expression (7), $\tau$ is a correlation time delay, $T_c$ is a chip bandwidth of the PRN code, for example, for a GPS C/a code, the $T_c$ is 1 ms. Then, the waveform of the correlation power of the direct signal at time t and the waveform of the correlation power of the reflected signal at different soil humidities are shown in FIG. 5.

Figure 5:
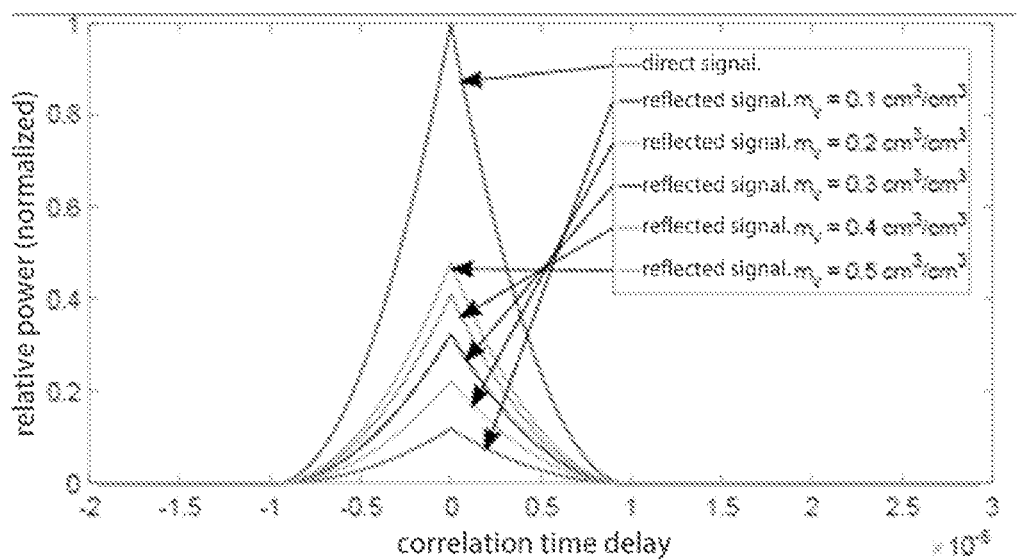
FIG. 5 is a schematic diagram of waveforms of correlation powers of direct and reflected signals according to the present disclosure.

In FIG. 5, the relative magnitudes of the correlation powers of the direct and reflected signals are determined by the reflectivity $\Gamma_{rl}(\theta)$ at time t when the elevation angle $\theta(t)$ of the navigation satellite is 40°, i.e.:

$$\frac{P_{rl}(t)}{P_d(t)} = \frac{\text{MAX}(P_{rl}(t))}{\text{MAX}(P_d(t))} = \Gamma_d(\theta) \quad (8)$$

Figure 6:
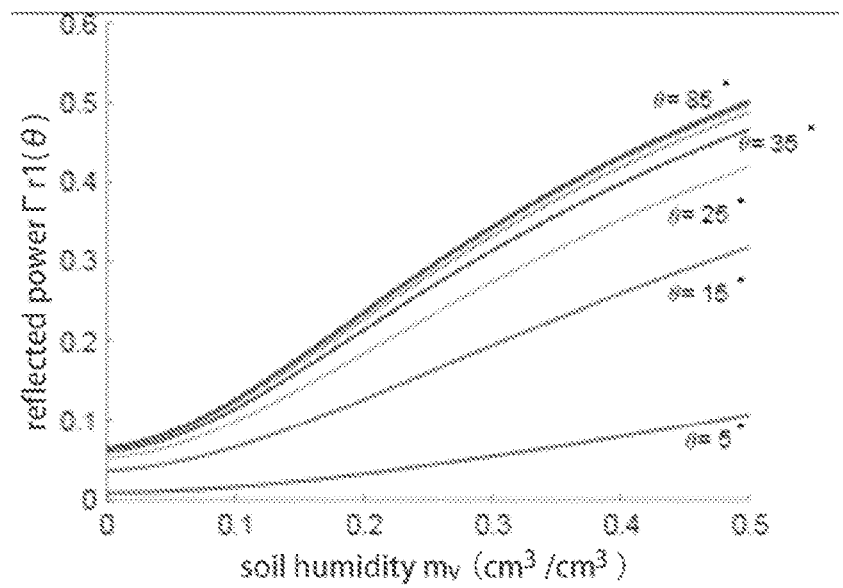
FIG. 6 is a schematic diagram of relationships between reflectivity and soil humidity at different elevation angles according to the present disclosure.

In expression (8), MAX (•) means calculating a peak of the correlation power, $F_{rl}(\theta)$ is given by expression (6). A change in soil humidity results in a change in the correlation power of the reflected signal according to a relationship among $F_{rl}$, $\varepsilon_r$, and $m_v$. FIG. 6 shows the variation of $\Gamma_{rl}$ with the soil humidity $m_v$ at different satellite elevation angles.

The soil humidity inverting module may then obtain the soil humidity by using table lookup method to perform inversion according to FIG. 6, after obtaining the correlation power of the direct and reflected signals.

Example 5

A method of soil humidity microwave remote sensing device with multi-mode compatibility via GNSS-R includes three-antenna discrete mode.

In this mode, the position calculating and controlling module control the switches to close contacts 1, 6, 8, 9, to enable the direct RHCP antenna, the reflective LHCP antenna, and the reflective RHCP antenna. In this case, the direct signal is subject to the processes of the preamplifier, the down-conversion module, the sampling and quantizing module, and the capturing and closed-loop tracking module in order, to obtain information about the code phase, the carrier phase, and correlation power of the direct signal. The information of the code phase and the carrier phase is used to assist the open-loop tracking module to perform the open-loop tracking on the LHCP component of the reflected signal and the RHCP component of the reflected signal, so as to obtain the correlation power information of the LHCP component of the reflected signal and the RHCP component of the reflected signal. After that, the position calculating and controlling module uses the direct signal to calculate position to obtain the position information of the device and the information of elevation angle and azimuth angle of the visible navigation satellites. Finally, the soil humidity inverting module performs inversion process on the correlation power information of the direct signal, the correlation power information of the LHCP component of the reflected signal, and the correlation power information of the RHCP component of the reflected signal to obtain the soil humidity.

In the mode, the soil humidity inverting module can perform soil humidity inversion by fully utilizing information carried by the reflection signals of different polarizations. Assuming that the correlation power of direct signal measured by the device is represented by $P_d(t)$, the correlation power of the LHCP component of the reflected signal measured by the device is represented by $P_{rl}(t)$, and the correlation power of the RHCP component of the reflected signal measured by the device is represented by $P_{rr}(t)$, the relative magnitudes of the correlation powers of the three signals on the conditions that the soil humidity is low (0.1 cm³/cm³) and is high (0.5 cm³/cm³) are shown in FIG. 7.

Figure 7:
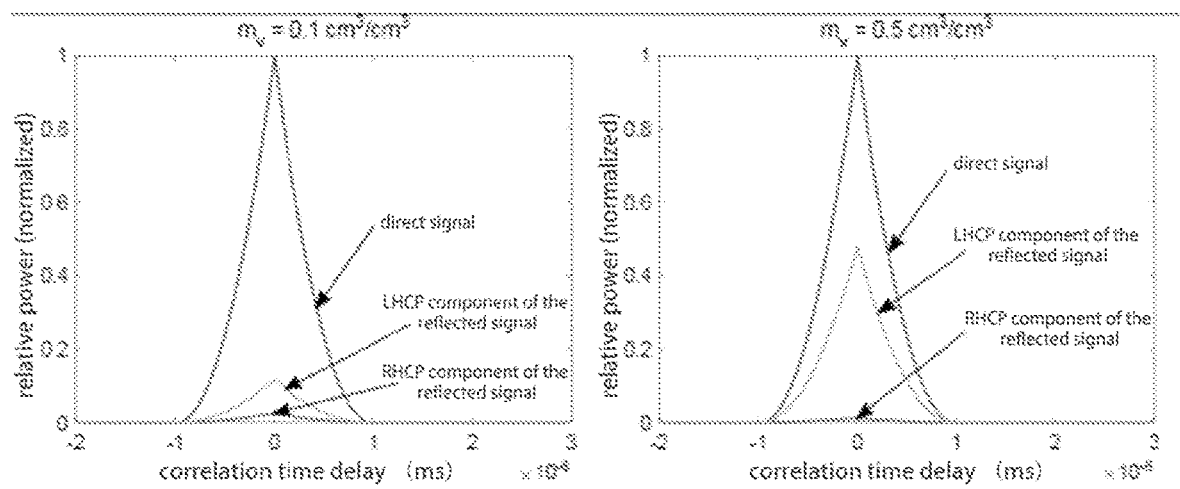
FIG. 7 is a schematic diagram of a comparison among the relative magnitude of correlation power of three signals under different soil humidity conditions according to the present disclosure.

In FIG. 7, it is assumed that the elevation angle of the navigation satellite is 40°, it can be seen from the figure that the larger the soil humidity is, the larger a difference between the powers of the RHCP component and the LHCP component of the reflected signal is. Therefore, the soil humidity inversion module can perform soil humidity inversion by using the power difference, the principle is as follows.

Power ratio $\Gamma$ of different polarization components of the reflected signal may be expressed as:

$$\Gamma(\theta) = \frac{P_{rr}}{P_{rl}} = \frac{P_{rr}/P_d}{P_{rl}/P_d} = \frac{\Gamma_{rr}(\theta)}{\Gamma_{rl}(\theta)} \quad (9)$$

Using the expressions (3) and (6), we can get:

$$\Gamma(\theta) = \frac{\cos^4(\theta)}{\sin^2(\theta)(\varepsilon_r - \cos^2(\theta))} \quad (10)$$

Since $\Gamma(\theta)$ is associated with the relative permittivity of soil, which is a function of soil humidity $m_v$, soil humidity inversion can be performed using $\Gamma(\theta)$. Further, soil roughness has the same effect on the RHCP component and the LHCP component of the reflected signal, so the $\Gamma_{rr}(\theta)$ and $F_{rl}(\theta)$ each are multiplied by the same coefficient, and the coefficient can be eliminated during calculating the power ratio of different polarization components, as shown in expression (9). Therefore, the soil roughness has little effect on the measurement of the soil humidity in the three antenna discrete mode. At different elevation angles, the relationships between $\Gamma(\theta)$ and m are shown in FIG. 8.

Figure 8:
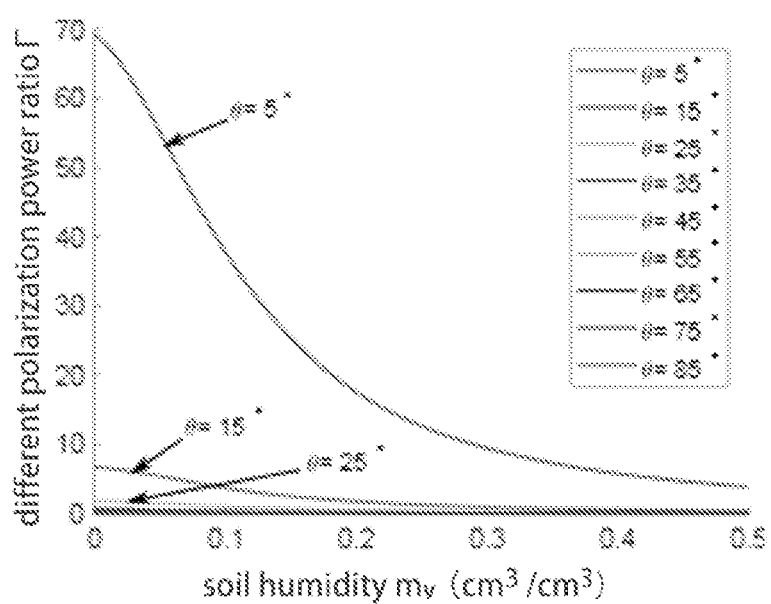
FIG. 8 is a schematic diagram of relationships between different polarization power ratios and different soil humidities according to the present disclosure.

The soil humidity inverting module may perform soil humidity inversion using a table look up method according to FIG. 8.

What is claimed is:

1. A soil humidity microwave remote sensing device with multi-mode compatibility via Global Navigation Satellite System-Reflectometry (GNSS-R) comprising:
   a direct right-hand circularly polarized (RHCP) antenna configured for receiving a GNSS direct signal from a satellite;
   a reflective RHCP antenna configured for receiving a right-handed component signal of a GNSS signal reflected by soil;

a reflective left-hand circularly polarized (LHCP) antenna configured for receiving a left-handed component signal of the GNSS signal reflected by the soil;

a combiner configured for summing the signals from the direct RHCP antenna, the reflective RHCP antenna, and the reflective LHCP antenna;

switches configured for being controlledly switched to enable the direct RHCP antenna, the reflective RHCP antenna, and the reflective LHCP antenna to be switched;

preamplifiers configured for performing power amplification and noise suppression on signals captured by the direct RHCP antenna, the reflective RHCP antenna, and the reflective LHCP antenna, which are analog radio frequency signals;

down-conversion modules configured for downconverting the analog radio-frequency signals to analog intermediate-frequency signals;

sampling and quantizing modules configured for converting the analog intermediate frequency signals into digital intermediate frequency signals;

a capturing and closed-loop tracking module configured for processing a digital intermediate frequency signal associated with the GNSS direct signal to measure parameters of the digital intermediate frequency signal associated with the GNSS direct signal and demodulate a navigation message and outputting the measured parameters to open-loop tracking modules;

open-loop tracking modules configured for tracking the digital intermediate-frequency signal associated with the right-handed component signal or the left-handed component signal and measuring correlation power;

a position calculating and controlling module configured for calculating positions of the device and the satellite by utilizing information received from the capturing and closed-loop tracking module, and controlling switching of the switches according to predetermined parameters so as to flexibly switching among different working modes; and soil humidity inverting modules configured for measuring a soil humidity by the measured signal.

2. The soil humidity microwave remote sensing device with multi-mode compatibility via GNSS-R according to claim 1, wherein the direct RHCP antenna is an omnidirectional antenna, wherein the reflective RHCP antenna is a high-gain, narrow-beam antenna, and wherein the reflective LHCP antenna is a high-gain, narrow-beam antenna.

3. A method of using the soil humidity microwave remote sensing device with multi-mode compatibility via GNSS-R according to claim 1, the method comprising:

in a single-antenna interference mode,
controlling the switches by the position calculating and controlling module to disable the reflective RHCP antenna and the reflective LHCP antenna, and only enable direct RHCP antenna;
passing an interference signal through corresponding one of the preamplifiers, corresponding one of the down-conversion modules, corresponding one of the sampling and quantizing modules, and the capturing and closed-loop tracking module in sequence to obtain power information of the interference signal;
performing position calculation by the position calculating and controlling module using the interference signal to obtain position information of the device and information about an elevation angle and an azimuth angle of the satellite; and performing an inversion process on the power information of the interference signal by the soil humidity inverting module to obtain a soil humidity, in a dual-antenna interference mode,
controlling the switches by the position calculating and controlling module to enable the reflective LHCP antenna and the direct RHCP antenna;
passing the GNSS direct signal and the left-handed component signal through the combiner to obtain an interference signal;
passing the interference signal through corresponding one of the preamplifiers, corresponding one of the down-conversion modules, corresponding one of the sampling and quantizing modules, and the capturing and closed-loop tracking module in sequence to obtain power information of the interference signal;
performing position calculation by the position calculating and controlling module using the interference signal to obtain position information of the device and information about an elevation angle and an azimuth angle of the satellite; and performing an inversion process on the power information of the interference signal by the soil humidity inverting module to obtain a soil humidity, in a dual-antenna discrete mode,
controlling the switches by the position calculating and controlling module to enable the reflective LHCP antenna and the direct RHCP antenna;
passing the GNSS direct signal through corresponding one of the preamplifiers, corresponding one of the down-conversion modules, corresponding one of the sampling and quantizing modules, and the capturing and closed-loop tracking module in sequence to obtain a code phase, a carrier phase, and correlation power information of the GNSS direct signal, wherein the code phase and the carrier phase are used to assist the open-loop tracking module in tracking the left-handed component signal in an open-loop manner to obtain correlation power information of the left-handed component signal;
performing position calculation by the position calculating and controlling module using the GNSS direct signal to obtain position information of the device and information about an elevation angle and an azimuth angle of the satellite; and
performing an inversion process on the correlation power information of the GNSS direct signal and the correlation power information of the left-handed component signal by the soil humidity inverting module to obtain a soil humidity, or in a three-antenna discrete mode,
controlling the switches by the position calculating and controlling module to enable the direct RHCP antenna, the reflective LHCP antenna, and the reflective RHCP antenna;
passing the GNSS direct signal through corresponding one of the preamplifiers, corresponding one of the down-conversion modules, corresponding one of the sampling and quantizing modules, and the capturing and closed-loop tracking module in sequence to obtain a code phase, a carrier phase, and correlation power information of the GNSS direct signal, wherein the code phase and the carrier phase is used to assist the open-loop tracking module in tracking the right-handed component signal and the left-handed component signal in an open-loop manner to obtain correlation power information of the right-handed component signal and correlation power information of the left-handed component signal;

performing position calculation by the position calculating and controlling module using the GNSS direct signal to obtain position information of the device and information about an elevation angle and an azimuth angle of the satellite; and performing an inversion process on the correlation power information of the GNSS direct signal, the correlation power information of the left-handed component signal, and the correlation power information of the right-handed component signal by the soil humidity inverting module to obtain a soil humidity.

* * * * *